(12) United States Patent
Zappia et al.

(10) Patent No.: US 9,949,615 B2
(45) Date of Patent: Apr. 24, 2018

(54) SYSTEMS AND METHODS FOR PREVENTING LASER FIBER MISFIRING WITHIN ENDOSCOPIC ACCESS DEVICES

(75) Inventors: Thomas Zappia, West Boylston, MA (US); Brian MacLean, Westford, MA (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 1204 days.

(21) Appl. No.: 13/599,929

(22) Filed: Aug. 30, 2012

(65) Prior Publication Data

US 2013/0072753 A1 Mar. 21, 2013

Related U.S. Application Data

(60) Provisional application No. 61/537,263, filed on Sep. 21, 2011.

(51) Int. Cl.
| | | |
|---|---|---|
| *A61B 1/00* | (2006.01) | |
| *A61B 1/018* | (2006.01) | |
| *A61B 5/06* | (2006.01) | |
| *A61B 17/00* | (2006.01) | |
| *A61B 1/05* | (2006.01) | |

(52) U.S. Cl.
CPC ........ *A61B 1/0008* (2013.01); *A61B 1/00147* (2013.01); *A61B 5/06* (2013.01); *A61B 5/068* (2013.01); *A61B 1/018* (2013.01); *A61B 1/05* (2013.01); *A61B 2017/00296* (2013.01)

(58) Field of Classification Search
CPC . A61B 1/00039; A61B 1/0008; A61B 1/0051; A61B 1/018; A61B 1/05; A61B 2017/00296

USPC ................................ 600/103, 104, 108, 146
See application file for complete search history.

(56) References Cited

U.S. PATENT DOCUMENTS

| | | | | |
|---|---|---|---|---|
| 5,193,526 A | * | 3/1993 | Daikuzono | ..................... 606/15 |
| 5,957,916 A | * | 9/1999 | Jeevanandam et al. | ........ 606/15 |
| 6,289,229 B1 | * | 9/2001 | Crowley | ...................... 600/310 |

(Continued)

FOREIGN PATENT DOCUMENTS

| | | | |
|---|---|---|---|
| JP | 54 066487 U | | 5/1979 |
| JP | 54066487 | * | 5/1979 |

(Continued)

OTHER PUBLICATIONS

International Search Report for International Patent Application No. PCT/US2012/053164 dated Dec. 14, 2012, 4 pages.

(Continued)

*Primary Examiner* — John P Leubecker
*Assistant Examiner* — Arnaldo Torres Diaz
(74) *Attorney, Agent, or Firm* — Bookoff McAndrews, PLLC

(57) ABSTRACT

A system for preventing inadvertent actuation of a medical device. The system includes an elongate tube having a proximal end, a distal end, and a lumen extending from the proximal end to the distal end. The lumen is configured to receive a medical device configured to transition between an actuated state and an inactive state. The device further includes a detection system configured to determine a position of a distal end of the medical device relative to the distal end of the elongate tube. The detection system includes a transmitting element and a receiving element.

15 Claims, 8 Drawing Sheets

(56) References Cited

U.S. PATENT DOCUMENTS

| | | | |
|---|---|---|---|
| 8,025,661 B2* | 9/2011 | Arnold et al. | 606/41 |
| 8,449,455 B2* | 5/2013 | Honda et al. | 600/118 |
| 8,632,461 B2* | 1/2014 | Glossop | 600/205 |
| 2003/0040737 A1* | 2/2003 | Merril et al. | 606/1 |
| 2005/0055174 A1* | 3/2005 | David et al. | 702/152 |
| 2007/0249901 A1* | 10/2007 | Ohline et al. | 600/117 |
| 2008/0071215 A1* | 3/2008 | Woods et al. | 604/116 |
| 2008/0255413 A1* | 10/2008 | Zemlok et al. | 600/106 |
| 2009/0123111 A1* | 5/2009 | Udd | 385/13 |
| 2009/0163769 A1* | 6/2009 | Robertson et al. | 600/109 |
| 2009/0177191 A1* | 7/2009 | Brown | 606/12 |
| 2009/0198104 A1 | 8/2009 | Sugiyama | |
| 2009/0299136 A1* | 12/2009 | Hasegawa et al. | 600/106 |
| 2009/0318797 A1* | 12/2009 | Hadani | 600/424 |
| 2010/0016757 A1* | 1/2010 | Greenburg et al. | 600/562 |
| 2010/0041949 A1* | 2/2010 | Tolkowsky | 600/109 |
| 2010/0125285 A1* | 5/2010 | Sewell et al. | 606/130 |
| 2011/0144479 A1* | 6/2011 | Hastings et al. | 600/424 |
| 2011/0190746 A1* | 8/2011 | Rink et al. | 606/12 |
| 2011/0207997 A1* | 8/2011 | Greenburg et al. | 600/104 |
| 2011/0275889 A1* | 11/2011 | Kase et al. | 600/103 |
| 2011/0295110 A1* | 12/2011 | Manzke et al. | 600/424 |
| 2011/0301414 A1* | 12/2011 | Hotto et al. | 600/114 |
| 2012/0083654 A1* | 4/2012 | Cooper et al. | 600/106 |
| 2014/0066705 A1* | 3/2014 | Robertson et al. | 600/103 |
| 2014/0343408 A1* | 11/2014 | Tolkowsky | 600/424 |

FOREIGN PATENT DOCUMENTS

| | | | | |
|---|---|---|---|---|
| JP | 2000 152913 A | | 6/2000 | |
| JP | 2000152913 A | * | 6/2000 | A61B 1/04 |
| JP | 2006 130183 A | | 5/2006 | |
| JP | 2006130183 A | * | 5/2006 | |
| JP | 2008 245877 A | | 10/2008 | |

OTHER PUBLICATIONS

International Preliminary Report on Patentability and Written Opinion issued in PCT International Application No. PCT/US2012/053164 dated Apr. 3, 2014 (8 pages).

* cited by examiner

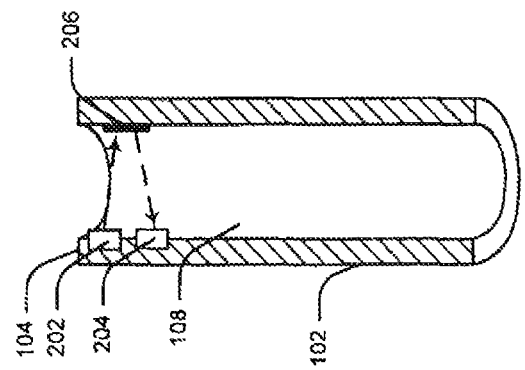
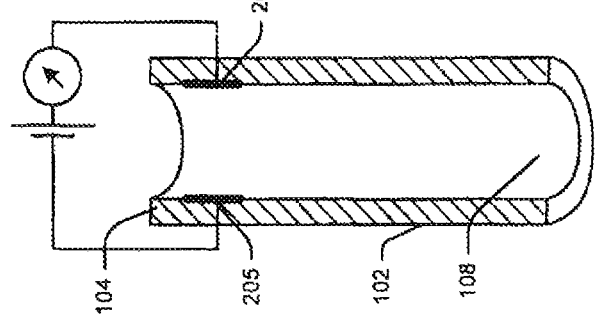
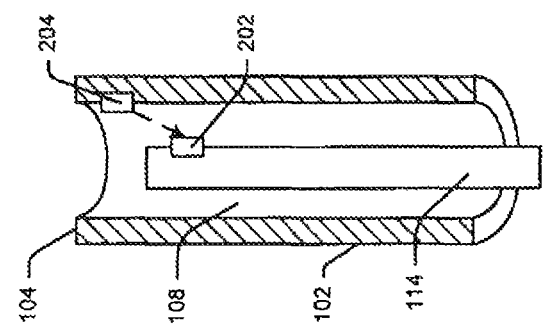
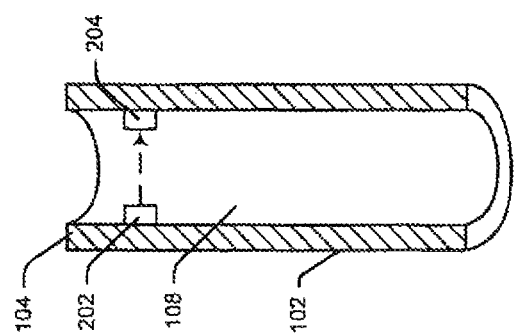

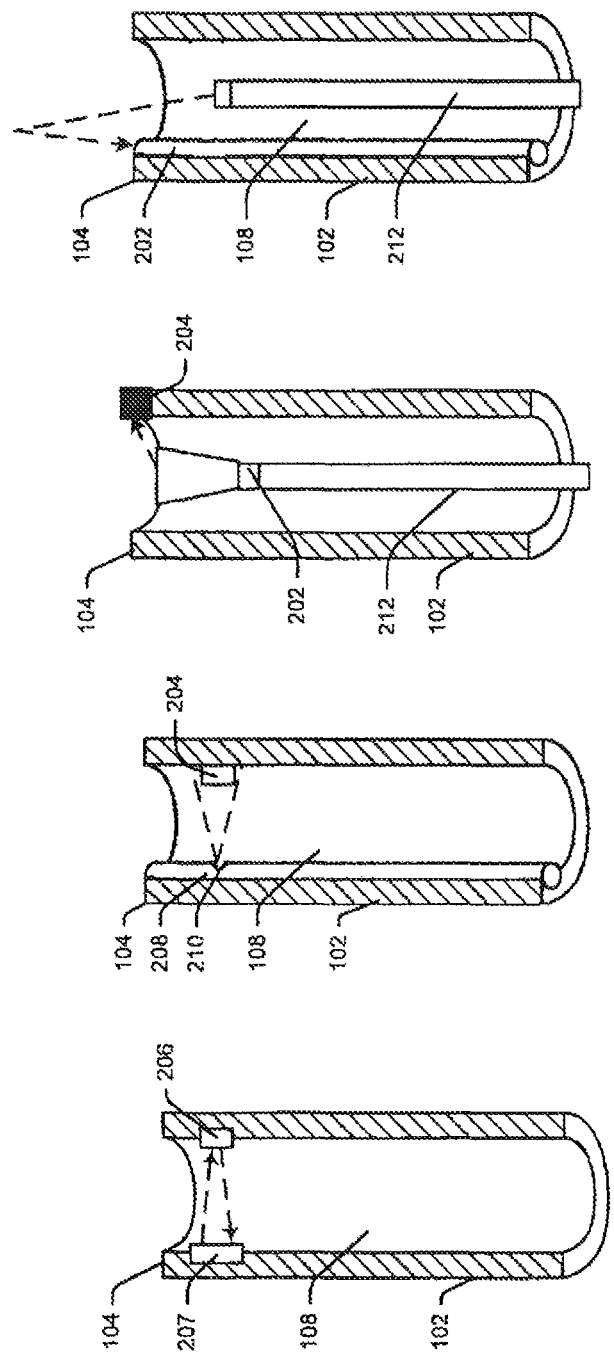

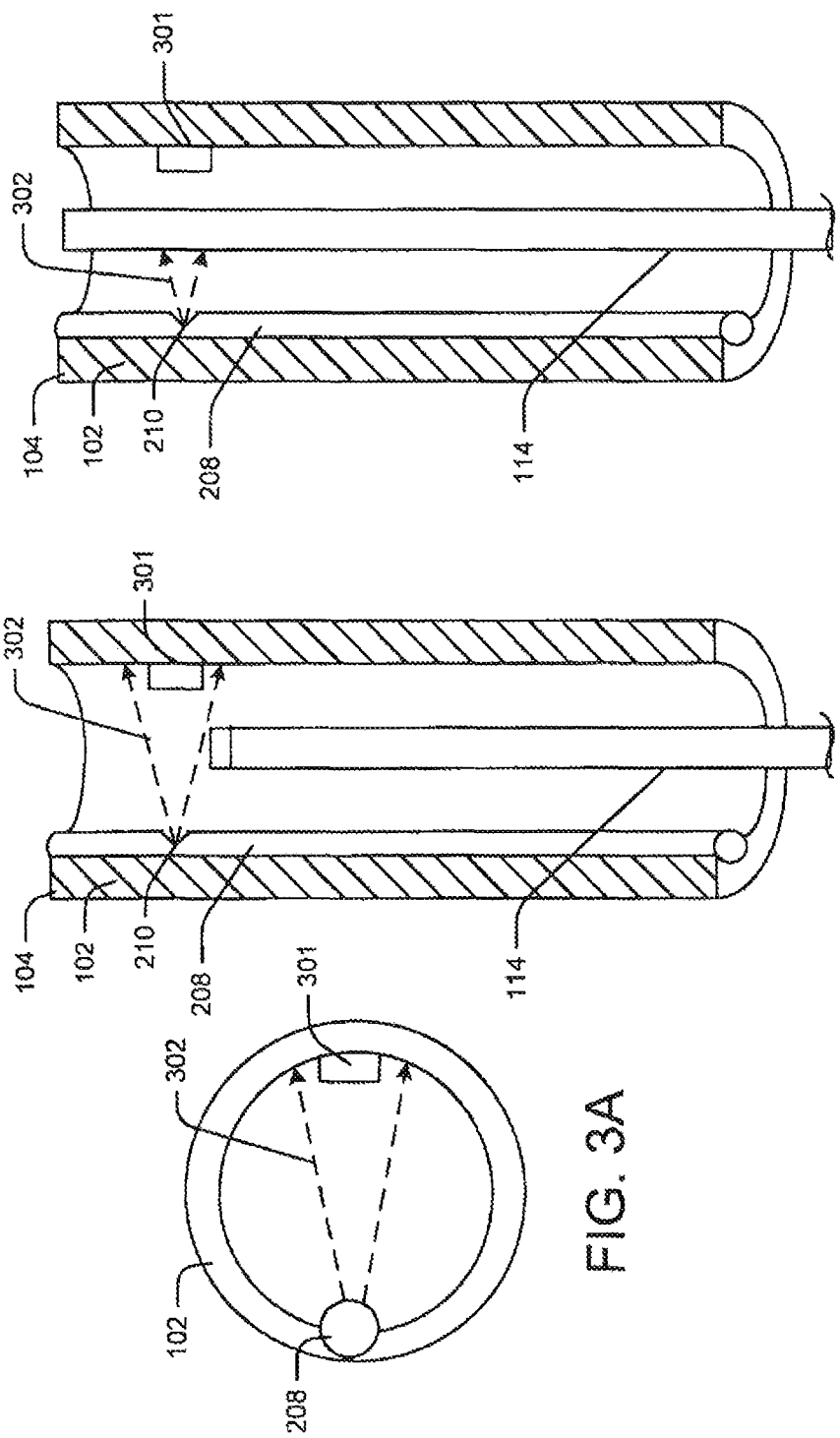

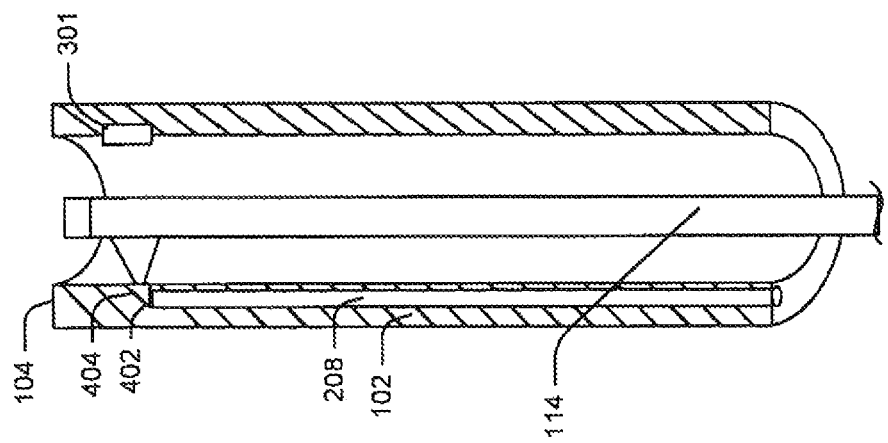
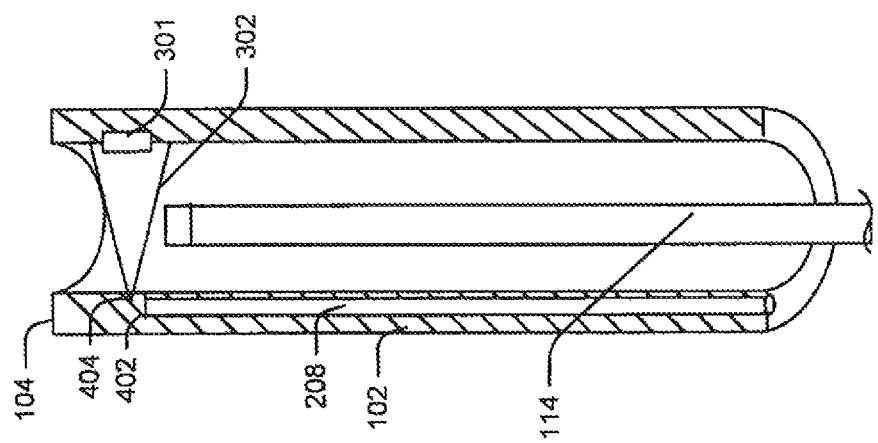

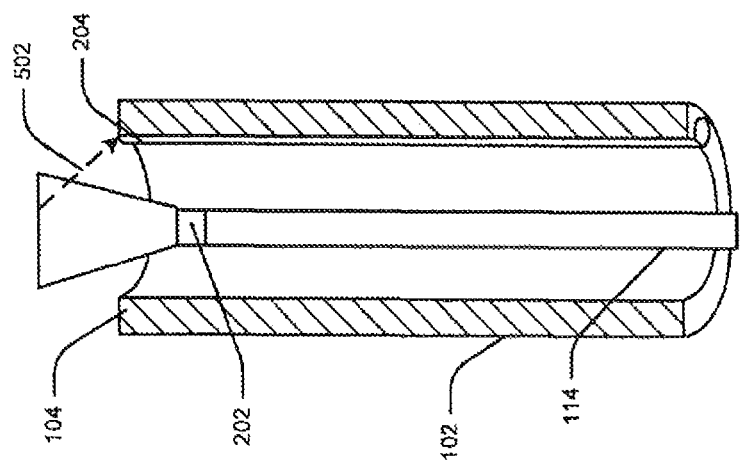
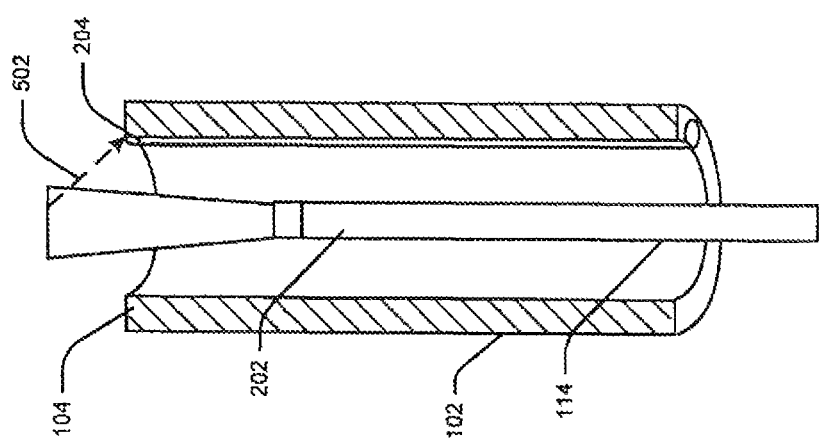

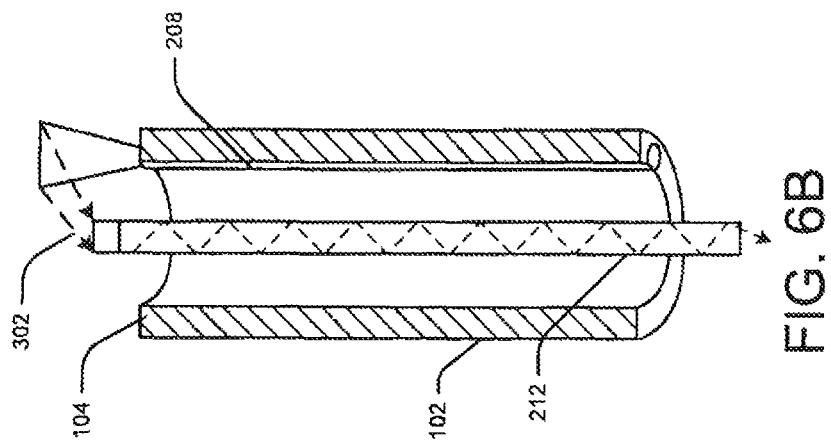
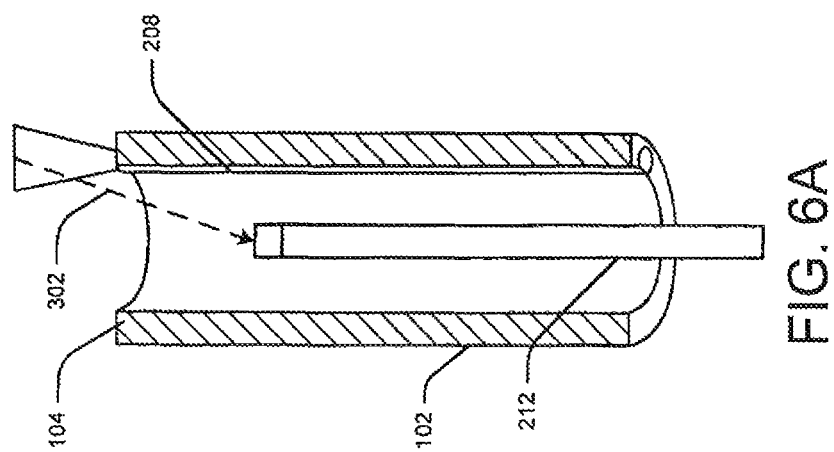

SYSTEMS AND METHODS FOR PREVENTING LASER FIBER MISFIRING WITHIN ENDOSCOPIC ACCESS DEVICES

CROSS-REFERENCE TO RELATED APPLICATION

This patent application claims the benefits of priority under 35 U.S.C. § § 119-120 to U.S. Provisional Application No. 61/537,263, filed on Sep. 21, 2011, the entirety of which is incorporated herein by reference.

FIELD OF THE INVENTION

Embodiments of the present disclosure relate generally to medical devices. In particular, embodiments of the instant disclosure relate to methods and systems for preventing misfiring of medical devices, such as, e.g., laser fibers, within endoscopic access devices.

BACKGROUND OF THE INVENTION

An endoscopic access device is typically a flexible tube inserted into a patient through a natural opening or a percutaneous incision to visualize and perform certain procedures. From time to time, various medical devices such as snares, pincers, morcellators, forceps, scopes, or baskets are introduced through the proximal opening of the endoscopic device to perform medical procedures inside a patient's body. Moreover, light sources, cameras, and other scopes may also be introduced through the endoscopic device from time to time to illuminate organs, capture images, or view organ properties.

Often, in minimally invasive surgery, laser devices are used to cauterize, fragment, or excise tissue and/or other masses within a patient's body. The laser is introduced through the endoscopic device once the device has been positioned proximal a desired surgical site. The laser fiber tip is extended from the distal end of the endoscopic device and then fired. Sometimes, however, it is difficult to determine the laser's exact position with respect to the endoscopic device. Thus, it is likely that the laser might fire while it is still inside the endoscopic device, potentially damaging the instrument. Moreover, during operations, the laser device may inadvertently be displaced, pushing the laser tip back into the endoscopic device tube while the laser is still functioning, potentially damaging the endoscopic device.

In recent years, one major repair cost incurred by endoscopic operators stems from lasers misfiring during procedures. In an attempt to prevent the laser from firing at the wrong time, a recent technique captures images of the laser head using a camera located at the endoscopic device's distal tip. The laser head is fired only when the operator can see the laser head protruding from the endoscopic device. Though this technique can solve the problem, it adds overhead and size—the camera and associated electronics. In most minimally invasive procedures, space is a major constraint. For example, in cholangioscopy, the endoscopic device is inserted through a small urethral opening, requiring a very small endoscopic device. Scientists continuously work towards inventing devices that are small enough to fit in these tiny spaces. Adding a space requirement for a camera merely to determine the position of the laser device reduces the space available for other devices and increases cost.

Therefore, there exists the need for a laser position detection system that does not utilize much space in the working channel and still helps prevent laser misfiring.

SUMMARY OF THE INVENTION

Embodiments of the present disclosure are related to systems and methods for preventing inadvertent actuation of a medical device while it is still within a lumen of an endoscopic device.

One embodiment of the present disclosure is directed to a system for preventing inadvertent actuation of a medical device. The system includes an elongate tube having a proximal end, a distal end, and a lumen extending from the proximal end to the distal end. The lumen is configured to receive a medical device configured to transition between an actuated state and an inactive state. The device further includes a detection system configured to determine a position of a distal end of the medical device relative to the distal end of the elongate tube. The detection system includes a transmitting element and a receiving element.

In various embodiments, the medical device may include one or more of the following additional features: the transmitting element is an energy source and the receiving element is a corresponding sensor; the transmitting element is disposed on a distal portion of the elongate tube, and the receiving element is disposed on a distal portion of the medical device; the transmitting element and the receiving element are disposed on a wall of the lumen; the elongate tube includes an endoscope having an illumination system; a portion of the illumination system is the transmitting element; the elongate tube is further configured to divert a portion of light energy from the illumination system to the receiving element; when a distal end portion of the medical device protrudes from a lumen of the elongate tube, the detection system is configured to generate a signal indicative of the position of the medical device; and the signal further controls activation of the medical device.

Another embodiment of the present disclosure is directed to a system for determining the position of a medical device. The system includes an elongate tube having a proximal end, a distal end, and a lumen extending from the proximal to distal end. The lumen may be defined by an internal wall of the elongate tube, and the medical device may be slidably positioned within the lumen. Further, the elongate tube may include an illumination element disposed between the internal wall and an external wall of the elongate tube. the medical device further includes a geometric feature disposed at a first location of the internal wall. The geometric feature is configured to deflect a portion of light energy from the illumination element to a sensor disposed at a second location of the internal wall. The second location may be opposite the first location, and the medical device may be configured to move between a first position and a second position. When the medical device is in the first position, a distal end of the medical device may be disposed proximally of the first and second locations, and, when the medical device is in the second position, the distal end of the medical device is disposed distally of the first and second locations. Moreover, a portion of the medical device may obstruct the light energy from the illumination element to the sensor.

In various embodiments, the medical device may include one or more of the following additional features: the medical device is a laser; the sensor is configured to generate a first signal when the sensor senses light from the illumination element; the sensor is configured to generate a second signal when the sensor does not sense light from the illumination element; and actuation of the medical device is prevented when the sensor is generating the first signal.

Another embodiment of the present disclosure is directed to a method of determining a position of a laser medical device within a lumen of an endoscopic access device. The endoscopic access device includes a light source. The method includes the steps of sensing an intensity of light reflected from one of the light source and the laser medical device, and comparing the sensed intensity to predetermined threshold intensity. Further, the method includes the steps of generating a first signal indicative of a first position of the medical device is the sensed intensity is below the predetermined threshold intensity.

In various embodiments, the medical device may include one or more of the following additional features: sensing the intensity of light includes sensing light reflected from the light source; the step of sensing is accomplished by a sensor located on the laser medical device; sensing the intensity of light includes sensing light reflected from the laser medical device, and the step of sensing is accomplished by a sensor located on the access device; the light reflected from the laser medical device includes light reflected from an aiming beam of the laser medical device; generating a second signal indicative of a second position of the medical device if the sensed intensity is above the predetermined threshold value; the second position corresponding to a distal end of the laser medical device protruding from the lumen of the access sheath.

Additional objects and advantages of the present disclosure will be set forth in part in the description, which follows, and in part will be obvious from the description, or may be learned by practice of the present disclosure. the objects and advantages of the present disclosure will be realized and attained by means of the elements and combinations particularly pointed out in the appended claims.

BRIEF DESCRIPTION OF THE DRAWINGS

The accompanying drawings, which are incorporated in and constitute a part of this specification, illustrate embodiments of the present disclosure and together with the description, serve to explain the principles of the embodiments described herein.

FIGS. 2A-2H illustrate various embodiments of a position detection system, according to embodiments of the present disclosure.

FIGS. 3A-3C are schematic views of an exemplary method for determining the position of a medical device with respect to an endoscopic device.

FIG. 4A-4B are schematic views of an exemplary embodiment for determining the position of a medical device with respect to an endoscopic device.

FIGS. 5A-5B are schematic views of an exemplary method for determining the position of a laser fiber with respect to an endoscopic device.

FIGS. 6A-6B are schematic views of an exemplary method for determining the position of a laser fiber with respect to an endoscopic device.

DESCRIPTION OF THE EMBODIMENTS

Reference will now be made in detail to embodiments of the present disclosure, an example of which is illustrated in the accompanying drawings. Wherever possible, the same reference numbers will be used throughout the drawings to refer to the same or like parts.

Overview

Embodiments of the present disclosure are directed to systems and methods for preventing medical devices, such as, e.g., laser fibers, lithotripters, cauterizing end-effectors, or other energized devices, from actuating while their distal tips are still within an endoscopic access device. To this end, embodiments of the present disclosure introduce a detection system that determines the position of a medical device with respect to the endoscopic device. Based on the position, the detection system may automatically actuate or prevent actuation of the medical device, or use an indicator to inform the operator whether it is safe to actuate the device or not. The medical device may be any device that may potentially damage itself or the endoscopic access device if actuated at the wrong time. Examples may include laser devices, pincers, cautery devices, morcellators, and baskets.

A signal transmitter and corresponding receiver are introduced in the distal end of the endoscopic device. For example, the transmitter and receiver may be located on opposite walls of a distal end portion of a lumen within an endoscopic access device. Alternatively, light source channels or the medical device itself operates as the transmitter or receiver. During normal operation, the transmitter continuously or intermittently emits signals detected by the receiver. When a medical device is inserted in the endoscopic access device and it reaches the distal end of the endoscopic device, the device may interrupt the normal signal received by the detector, prompting the detector to generate a "ready" signal. This signal indicates to the operator that the device is positioned at the distal end of the endoscopic device and in a position to safely actuate the device.

In this disclosure, embodiments of the system are described using an endoscope. It will be understood, however, that the system and method may be incorporated in a similar device, such as a uteroscope, duodenoscope, cholangioscope, or any suitable endoscopic access device without departing from the scope of the present disclosure. Moreover, embodiments of the present disclosure are described using an exemplary medical device—a laser unit. These embodiments, however, may be implemented to detect the position of any suitable device with respect to the scope's distal end. For example, some devices such as baskets, expandable meshes, pincers, snares, or malecots actuate once they exit the endoscopic device. If these devices are actuated while still in the endoscopic tube, they may damage themselves or the endoscopic device. It is therefore desirable to know the location of these devices relative to the endoscopic device as well.

Exemplary Embodiments

Figure 1:
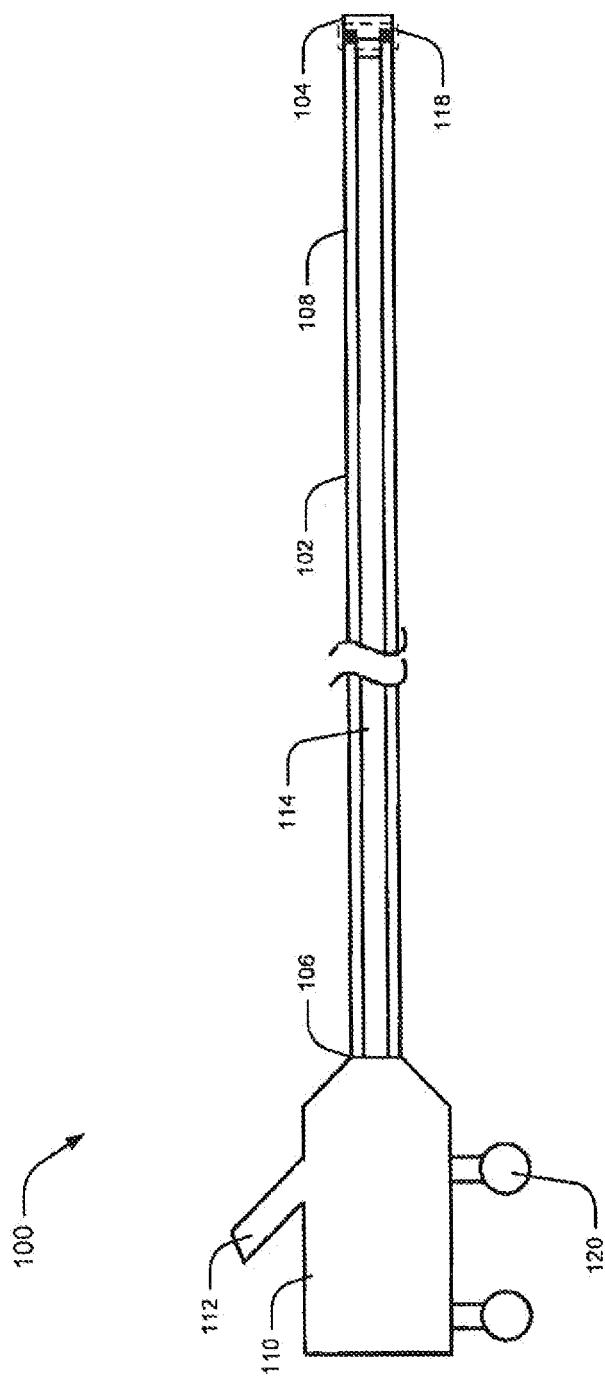
FIG. 1 is a perspective view of an endoscopic access device, according to an embodiment of the present disclosure.

FIG. 1 illustrates an exemplary endoscopic device 100 including an elongate tube 102 with a distal end 104, a proximal end 106, and a lumen 108 extending from the distal to proximal end. The device 100 further includes a handle 110 coupled to the proximal end 106, one or more ports 112 to insert medical devices (such as medical device 114) into the elongate tube 102, one or more working channels (not shown) and a location detection system 118. Moreover, handle 110 may include one or more control elements 120 to position and activate (e.g., steer) elongate tube 102 and the medical devices, respectively.

Tube 102 may be flexible, and it may include one or more internal channels for receiving medical devices, such as snares, pincers, baskets, imaging devices, or lasers. To traverse cavities in a patient's body, the tube 102 may have a cross-sectional configuration adapted to a desired body lumen. In the illustrated embodiment, tube 102 is generally circular, with a generally circular interior lumen 108. But, in other configurations, tube 102 may have an elliptical, irregular, semi-circular, or oval profile. Further, tube 102 may have a uniform diameter or it may taper at distal end 104 to allow convenient insertion within a patient's body.

Such flexible tubes may be formed of any suitable material having sufficient flexibility to traverse body cavities and tracts. Suitable materials may include synthetic plastics, fiber, or polymers. Alternatively, tube 102 may be rigid or semi-rigid, formed from materials such as stainless steel or the like, including shape memory alloys such as nitinol. Tube 102 may also be manufactured from any biocompatible material such as a sheath, with or without a Teflon outer layer.

Handle 110 may include control elements 120 to maneuver elongate tube 102 to the desired location and actuate medical device 114 once the tube is in place. Various mechanisms exist and any suitable technique may be utilized to maneuver tube 102 and actuate medical device 114. For example, controls 120 may be provided to provide translation and rotational motion to the tube's distal end 104, allowing it to turn along the natural curves of tortuous anatomical lumens. These maneuvering mechanisms are widely known in the art and not discussed here any further. Similarly, to actuate a medical device, such as a suction device, a laser, or a light source, the control element 120 may be a simple power switch. For devices that switch between a collapsed and expanded position, different actuation mechanisms may exist. For instance, the handle 110 may include a release button. Alternatively, handle 110 may include mechanical means, such as pulleys, levers, or pull threads to actuate medical device 114. As described in this disclosure, the term "actuate" refers to altering either mechanical or electrical state of a device for operation.

When medical devices are not an integral part of the endoscopic access device 100, but inserted through the port 112, their controls 120 may not be present on handle 110. Instead, the mechanism may be present on the handles of the inserted medical devices. These handles in turn may be coupled to the endoscopes handle 110, allowing an operator to operate the various devices with one hand and hold elongate tube 102 with the second hand.

In some embodiments, lumen 108 may be divided into two or more channels. Channels may allow operators to extend one or more medical devices through lumen 108 to distal end 104. Often multiple devices may be inserted into the endoscopic device 100 through the same channel. For example, light sources and cameras may be inserted together in lumen 108 without any adverse affects. In such cases, lumen 108 may include one channel. Alternatively, when a suction device or an irrigation device is used, lumen 108 may be divided into multiple channels; one for each medical device.

Medical devices may be introduced in the channels through proximal end 106. As described, devices may be inserted through ports 112 or they may be permanently attached to the tube's proximal end 106 or handle 110. In some endoscopic devices, specific medical devices are frequently used. For example, throughout a medical procedure, light sources and cameras may be required to illuminate and capture images of organs. In these cases, the fight source and camera may be permanently incorporated along the walls of lumen 108. When medical devices are required only for a short duration of the operation (for example a suction device may be required only to drain fluid present in a cavity or extract undesired masses), they may be introduced and removed through port 112.

In an inactive condition, the distal end of the medical devices may rest within the tube's lumen 108 shielded from the environment. In this state, the medical devices should ideally not be actuated. Sometimes, however, medical devices may be accidentally actuated within elongate tube 102, with possibly damaging results. Moreover, because endoscopic device 100 lies within a patient's body during the procedure, operators often find it difficult to determine whether the medical device's end remains within lumen 108 or extends beyond it. Consequently, operators may actuate the device prematurely, and thereby irrevocably damage the devices as well as the elongate tube 102. Embodiments of the present disclosure introduce detection system 118 that aids operators in determining whether the distal end (often termed "end-effector") of the medical device 114 is within the lumen 108 or extending out of it, and consequently preventing misfiring.

The detection system 118 includes a transmitter and a receiver. Transmitter may generate one or more signals. Signals include electrical, optical, infrared, x-ray, acoustic, or other such suitable signals. For instance, the transmitter may be a light source, such as an LED transmitting optical signals. Alternatively, the transmitter may be a fluorescent material emitting light of a particular wavelength. Similarly, other transmitter devices that generate one or more signals may be contemplated. Further, the transmitter may transmit these signals continuously, or intermittently.

The receiver detects signals generated by the transmitter. Depending on the transmitter used, the receiver may be selected. For example, in case the transmitter is a light source, the receiver may be a light sensor. Similarly, if the transmitter is an electrical generator, the receiver may be an electrical conductor. It will be understood that multiple combinations of transmitters and receivers are possible and they all lie within the scope of the present disclosure.

FIGS. 2A-2H illustrate exemplary detection systems placed in a distal portion of the elongate tube; more particularly, FIGS. 2A-2H are cut-away cross-sectional views of elongate tube 102 illustrating various exemplary embodiments of detection system 118, including a transmitter 202 and a receiver 204.

In FIG. 2A, the detection system 118 is positioned at or proximate the distal-most end 104 of the lumen 108. In other configurations, detection system 118 may be coupled to any part of elongate tube 102. For example, detection system 118 may be coupled to the distal rim or distalmost end-face of tube 102. Alternatively, multiple detection systems may be placed along portions of lumen 108.

If lumen 108 includes multiple channels, detection system 118 may be coupled to the distal ends of selected channels or all of the channels. Detection system 118 may not be coupled to some channels because actuation of certain medical device (such as a suction device) inside the elongate tube 102 may not necessarily result in any adverse effects. In those situations, monitoring the medical device's location or position may not be economical or required.

In other configurations, especially when elongate tube 102 tapers at distal end 104, two or more channels may merge into a single channel at the tube's distal end. That may be particularly true in endoscopic devices tailored to procedures that call for only one medical device at a time. In those implementations, detection system 118 may be mounted in the merged channel, reducing cost.

FIG. 2B illustrates an exemplary embodiment where one part of detection system 118 (either the receiver or the transmitter) is coupled to a distal portion of the medical device. The other part may be coupled to the lumen's distal end 104. When the transmitter or receiver placed on the medical device 114 comes in range of and/or passes the receiver or transmitter coupled to elongate tube 102, respectively, a signal may be generated.

Moreover, instead of being a transmitter-receiver pair, in some configurations, detection device 118 may be any suitable device that can detect the position of medical device 114. FIG. 2C illustrates, for example, detection system 118 including a pair of electro-conductive plates 205 disposed opposite each other on a distal portion of the tube 102. These plates behave like a capacitor when electric signals are passed through them. In addition, the space between the plates behaves like a dielectric medium. Any change in this medium alters the capacitance of plates 205.

Elements of detection system 118 may be within range of each other. For example, transmitter 202 and receiver 204 may be coupled to the inner wall opposite each other, permitting the signal from transmitter 202 to directly reach receiver 204. Alternatively, transmitter 202 and receiver 204 may be coupled along the same inner wall of elongate tube 102. FIG. 2D illustrates such an embodiment. Here, a signal reflecting device, such as a mirror 206 may be incorporated such that it reflects the signal from the source (i.e., transmitter 202) directly to the detector receiver 204). In some embodiments, transmitter 202 and receiver 204 may be a common transceiver device 207 performing operations of both the transmitter and receiver (FIG. 2E). In this case, strategically placed reflectors, e.g., reflector 206, may reflect beams generated by the transceiver 207 back to itself for detection. Moreover, in some cases, transmitter 202 may generate signals that fall on medical device 114 and the medical device may reflect the signal to receiver 204. In such cases, transmitter 202 and receiver 204 may be a common device or separate devices placed close to each other.

In other exemplary embodiments, existing devices or sources may be utilized as transmitters or receivers. FIG. 2F illustrates this embodiment. Here, a light source channel 208 embedded in the elongate member walls or present within the lumen 108, may function as the transmitter 202. A geometric feature, such as a small aperture 210 may be created in a distal portion of channel 208 to deflect a portion of the light beam into the lumen 108. The deflected light beam may fall on receiver 204 placed on a wall opposite the aperture 210.

In another embodiment, illustrated in FIG. 2G, the medical device 114, such as a laser unit 212, may serve as the transmitter. A suitable receiver 204 may be placed at the elongate tube's distal end 104 to measure the intensity of light emitted by the laser unit 212, or the intensity of light reflected from tissue. The detected intensity will vary in accordance with the position of the laser unit 212. Alternatively, the light source channel 208 may be the transmitter and a receiver 204 may be coupled to the distal end of the medical device to detect the intensity of light reaching the laser.

In some cases, the laser unit 212 may be the transmitter and the light source channel 208 may be the receiver or vice versa. The light source channel 208 and the laser unit 212 are typically made of an optical fiber with a source at its proximal end. Light or laser energy from the proximal end, is transmitted to the distal end through total internal reflection within the optical fiber. Using this concept, a portion of the light (e.g., a reflection off of bodily tissues) emanating from the distal end of the light source channel 208 may enter the laser unit 212 through the distal end opening. This embodiment is depicted in FIG. 2H. A sensor or receiver (not shown) attached to the proximal end of the light source channel 208 may sense the received light to determine the position of the laser unit 212 with respect to the elongate tube. If the laser unit 212 extends out of lumen 108, more light may enter through its distal opening, increasing the intensity of light detected at the receiver. Alternatively, if laser unit 212 is within lumen 108, less light enters through its distal opening, decreasing the intensity of light detected at the receiver.

Similarly, the light source channel 208 may act as a conduit to receive a portion of laser energy emitted by the laser unit 212. In these cases, an aiming beam may be included in the laser signal such that a light detector at the proximal end of the light source channel 208 can detect its intensity. Again, based on the position of the laser unit 212, the received intensity may change.

Using the light source channel 208 and the medical device as transmitters and receivers reduces costs and increases the available space inside the lumen 108. This embodiment may be utilized In small diameter endoscopic devices such as cholangioscopes, where space is usually a constraint. Various other placement configurations may be contemplated without departing from the scope of the present disclosure.

Receiver 204 may include a signal detector, a signal comparator, and an output module. The signal detector receives the transmitted signal and forwards it to the signal comparator. The comparator compares the input signal value with a preconfigured threshold value. If the input signal falls below a threshold value, the comparator may raise a signal, such as a "ready" signal, and provide the signal to the output module. The output module in turn notifies the operator or automatically actuates medical device 114. It will be understood that the "ready" signal is generated when the end-effector extends out of lumen 108 or is placed such that it would not damage the lumen even if it were actuated. For example, in some embodiments, a "ready" signal may be generated even if the distal end of medical 114 is not extending out of lumen 108.

Alternatively, the comparator may raise a signal as long as the input signal is above a threshold value. This signal, such as an "alert signal," may be provided to the output module, which generates an alert or automatically turns off medical device 114 until the alert signal is removed. It will be understood that the "alert" signal is generated when the end-effector (or a distal end portion) of medical device 114 is positioned such that it may potentially damage the lumen 108 if it were actuated.

To alert an operator, the ready or alert signals may be visual, auditory, or tactile signals informing the operator whether it is safe or unsafe to actuate medical device 114. In some embodiments, the output module may be an external device connected to receiver 204 through wired or wireless means. For example, the output module may be an LED mounted on handle 110. When medical device 114 blocks the signal, the comparator generates the ready signal, which may light the LED, informing the operator that it is safe to actuate medical device 114. Alternatively, the output module may be a speaker generating a sound signal corresponding to the ready signal. Similarly, the output module may generate a visual signal, such as a text or graphical message.

To automatically control operation of medical device 114, the output module may be connected to the actuation mechanism of medical device 114 through wired or wireless means. The ready signal, for example, may automatically actuate the medical device 114 and the alert signal may automatically deactivate or collapse medical device 114.

Exemplary Methods

The following sections describe the operation of detection system 118 using three exemplary detection systems.

In the first example, transmitter 202 is an LED source, and receiver 204 is an optical detector/sensor, such as detector 301. Typically, in endoscopic devices 100 a small light source channel 208 is incorporated longitudinally along the lumen wall or embedded in the tube wall. FIG. 3A is a distal end view of such an endoscopic device, FIG. 3B is a sectional side view with medical device 114 within the lumen, and FIG. 3C is a sectional view with a portion of medical device 114 extending out of lumen 108. In such devices, rather than mounting a separate transmitter, a small aperture 210 may be created in a distal portion of the light source channel 208. Light beams (generally depicted as light beams 302 in FIGS. 3A, 3B, and 3C) from the aperture 210 may enter lumen 108. Further, the aperture angle may be selected such that detector 301 coupled to the opposite wall may be in direct line-of-sight of aperture 210. Alternatively, the detector's position may be modified such that it is in direct line-of-sight with the aperture 210.

In another embodiment, the light source channel 208 may have certain built-in features to direct a light beam 302 from the light source to the optical detector. For instance, the distal end of the light source channel 208 may include tactically placed reflective surfaces such as mirrors that deflect a portion of the light beam 302 towards the detector 301. FIG. 4 illustrates such an embodiment. More particularly, FIG. 4A depicts medical device 114, such as laser unit 212 within lumen 108, and FIG. 4B depicts the medical device extending out of lumen 108. Here, light source channel 208 does not extend along the complete length of the tube 102; instead, it extends from the proximal end to a distal portion of tube 102. Moreover, light source channel 208 may be embedded in the tube wall and separated from lumen 108 by a thickness of material. Light source channel 208, however, may communicate with lumen 108 in one more locations. A notch 402 may be cut proximate the distal end of the light source channel 208 to deflect light from light source channel 208 into lumen 108. Moreover, a reflective surface 404 such as a mirror may be placed in the notch 402 such that light beam 302 from the light source channel enters the lumen 108. Detector 301 is placed on the wall opposite the notch 402 to detect light beams 302 emitting from the notch 402.

The operation of the embodiments illustrated in FIG. 3 and FIG. 4 is similar, and therefore will be described together in the following section.

Initially, when the laser unit 212 is not present near the tube's distal end 104, the light beam 302 continuously falls on the detector 301. FIG. 3B and FIG. 4A illustrate this embodiment. The detector 301 continuously or intermittently converts the light beam 302 into an electrical signal and compares this value with a threshold value. As described previously, the comparator may either raise an alert signal upon comparison or not raise any signal, because the input signal is above the threshold value. The laser unit 212 is not actuated at this stage, and an operator is aware that the end-effector is still within lumen 108.

When laser unit 212, however, reaches the distal end 104 (FIG. 3C and FIG. 4B), it may block some portion or all of light beam 302 falling on the detector 301. Consequently, detector 301 detects little or no light energy. The corresponding electrical signal may therefore be lower than the threshold value, causing detector 301 to raise a ready signal or stop the alert signal. Accordingly, the operator may actuate the laser unit 212 and begin the procedure or the output module may automatically actuate the laser.

During the procedure, if the laser unit 212 is accidently displaced or retracted back into elongate tube 102, it will no longer block the light beam 302. Consequently, detector 301 may once more raise the alert signal or stop the ready signal, signaling the operator to immediately power off the laser unit 212 or powering it off automatically.

Using detection system 118, inadvertent actuation of the medical device 114 may be eliminated, drastically increasing the life of the elongate tube 102.

FIGS. 5A-5B illustrate another exemplary detection method. Here medical device 114 (e.g., laser unit 212) is the transmitter, and the light source channel 208 or any other control unit, such as detector 301 may be the receiver. The laser signal includes an aiming beam (along with the infrared beam, the laser includes a light beam in the visible spectrum, which is commonly referred to as "aiming beam"). The intensity of aiming beam or its reflection 502 detected at the detector 301 may help to determine the location of the laser unit 212. Alternatively, a portion of the reflected aiming beam 502 may enter the light source channel 208 and reach the proximal end of the channel. Here, a detector (not shown) may measure the intensity of the aiming beam 502.

When laser head is within lumen 108, the intensity of the aiming beam 502 received at the laser unit 212 is lower than the beam's intensity when the laser head is extending out of lumen 108. Based on the detected intensity, detector 301 may generate a ready or alert signal. For example, if the detected intensity falls below a preconfigured threshold value, detector 301 may generate an alert signal.

Alternatively, laser unit 212 may not include an aiming beam. In this case, the endoscopic system 100 may incorporate a laser beam detector to detect reflected laser energy instead.

FIGS. 6A-6B illustrate another exemplary method for detecting the position of a laser unit with respect to the elongate tube. Here medical device 114 (e.g., laser unit 212), or a portion thereof, is the receiver, and light source channel 208 is the transmitter. A proximal portion of laser unit 212 may include a receiver (not shown). When the light source channel emits light, a portion of the light beam 302 may be reflected back towards the laser unit 212 and enter the laser unit's optical cavity. Light beam 302 travels proximally through the optical cavity to the proximal end of the laser unit 212. Here the attached receiver (not shown) may sense the light intensity.

When laser unit 212 is within lumen 108, lesser light reaches the receiver than when the distal end of the laser unit 212 extends out of the lumen. By comparing the detected light intensity with a preconfigured intensity threshold, the position of the laser unit 212 may be determined.

Alternatively, the distal end of the laser device may be configured to include a receiver (not shown). The receiver senses any light beams falling on the laser unit 212 and determines the position of the laser based on intensity of the received light beams.

In other embodiments, transmitter 202 may be in the form of a fluorescent coating (not shown) on a distal end portion of medical device 114, and receiver 204 may be in the form of a photo-detector (not shown) or other such detector system coupled to the lumen's distal end 104. When medical device 114 is within the lumen 108, it is not within the range of the photo-detector, and therefore it does not detect the fluorescence emitted by the fluorescent coating. Subsequently, when laser unit 212 extends towards distal end 104, the photo-detector senses the light emitted by the fluorescent coating, and generates a "ready" signal.

Figure 7A:
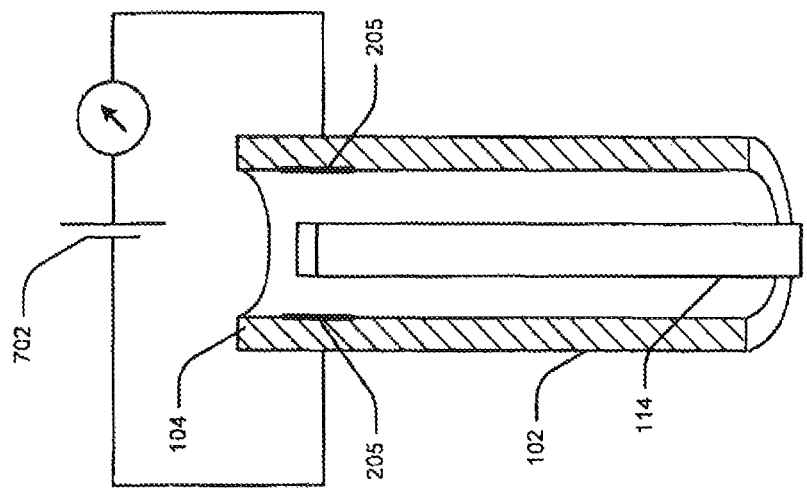
FIG. 7A-7B are schematic views of an exemplary method for determining the position of a medical device with respect to an endoscopic device.
Figure 7B:
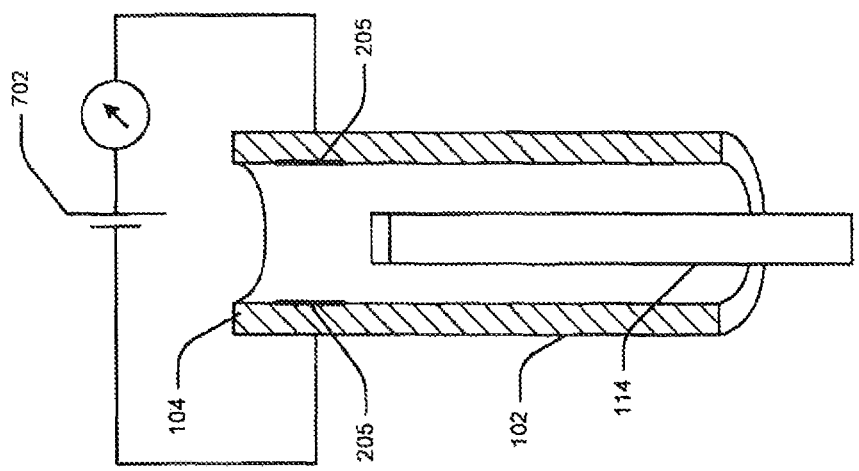

FIGS. 7A-7B illustrate yet another exemplary detection method. Here, the transmitter and receiver are embodied as two metallic plates 205 coupled to an electric source 702. Low intensity electricity is passed through metallic plates 205, allowing the plates to behave like the conductors of a capacitor and the space between the plates to behave like the dielectric medium. When medical device 114 is not present in lumen 108 between the plates 205, the exhibited capacitance is a certain value. When medical device 114 enters the space between plates 205, the capacitance changes. A comparator connected to electric plates 205 continuously compares the capacitance with a preconfigured value. When the capacitance crosses a threshold value, the output module generates an alert or ready signal.

It will be understood that the methods and detection systems described in this disclosure are merely exemplary and any other such detection system may be incorporated instead, that can determine the position of the medical device 114 with respect to the distal end 104.

Embodiments of the present disclosure may be used in various medical or non-medical procedures. In addition, certain aspects of the aforementioned embodiments may be combined with other aspects of the embodiments, or removed, without departing from the scope of the disclosure.

Other embodiments of the present disclosure will be apparent to those skilled in the art from consideration of the specification and practice of the embodiments disclosed herein. It is intended that the specification and examples be considered as exemplary only, with a true scope and spirit of the invention being indicated by the following claims.

What is claimed is:

1. A system for preventing inadvertent actuation of a medical device, the system comprising:
   a medical device comprising a laser and configured to transition between an actuated state and an inactive state;
   an elongate tube having a proximal end, a distal end, and a lumen extending from the proximal end to the distal end, the lumen configured to receive the medical device; and
   a detection system configured to determine a position of a distal end of the medical device relative to the distal end of the elongate tube, wherein the detection system includes a transmitting element disposed on a distal portion of the elongate tube and a receiving element disposed on a distal portion of the medical device.

2. The system of claim 1, wherein the transmitting element is an energy source and the receiving element is a corresponding sensor.

3. The system of claim 1, wherein the transmitting element comprises a light source.

4. The system of claim 1, wherein the elongate tube includes an endoscope having an illumination system.

5. The system of claim 4, wherein a portion of the illumination system is the transmitting element.

6. The system of claim 4, wherein the elongate tube is further configured to divert a portion of light energy from the illumination system to the receiving element.

7. The system of claim 1, wherein, when a distal end portion of the medical device protrudes from a lumen of the elongate tube, the detection system is configured to generate a signal indicative of the position of the medical device.

8. The system of claim 7, wherein the signal further controls activation of the medical device.

9. A system for determining the position of a medical device, the system comprising:
   a medical device comprising a laser;
   an elongate tube having a proximal end, a distal end, and a lumen extending therebetween, wherein the lumen is defined by an internal wall of the elongate tube, the medical device is slidably positioned within the lumen, and the elongate tube includes an illumination element disposed between the internal wall and an external wall of the elongate tube;
   a geometric feature disposed at a first location of the internal wall, wherein the geometric feature is configured to deflect a portion of light energy from the illumination element to a sensor disposed on the medical device, wherein the medical device is configured to move between a first position and a second position, wherein, when in the first position, a distal end of the medical device is disposed proximally of the first location, and, when in the second position, the distal end of the medical device is disposed distally of the first location.

10. The system of claim 9, wherein the sensor is configured to generate a first signal when the sensor senses light from the illumination element.

11. The system of claim 10, wherein the sensor is configured to generate a second signal when the sensor does not sense light from the illumination element.

12. The system of claim 10, wherein actuation of the medical device is prevented when the sensor is generating the first signal.

13. A method of determining a position of a laser medical device within a lumen of an endoscopic access device, the endoscopic access device including a light source, the method comprising:
   sensing an intensity of light reflected from the light source;
   comparing the sensed intensity to a predetermined threshold intensity; and
   if the sensed intensity is below the predetermined threshold intensity, generating a first signal indicative of a first position of the medical device;
   wherein the step of sensing is accomplished by a sensor located on the laser medical device.

14. The method of claim 13, wherein the method further includes the step of generating a second signal indicative of a second position of the medical device if the sensed intensity is above the predetermined threshold value.

15. The method of claim 14, wherein the second position corresponds to a distal end of the laser medical device protruding from the lumen of the access sheath.

* * * * *